US008320650B2

(12) United States Patent
Demos et al.

(10) Patent No.: US 8,320,650 B2
(45) Date of Patent: Nov. 27, 2012

(54) IN VIVO SPECTRAL MICRO-IMAGING OF TISSUE

(75) Inventors: Stavros G. Demos, Livermore, CA (US); Shiro Urayama, Davis, CA (US); Bevin Lin, Sacramento, CA (US); Ramez Moussa Ghobrial Saroufeem, Sacramento, CA (US)

(73) Assignees: Lawrence Livermore National Security, LLC, Livermore, CA (US); The Regents of the University of California, Oakland, CA (US)

( * ) Notice: Subject to any disclaimer, the term of this patent is extended or adjusted under 35 U.S.C. 154(b) by 587 days.

(21) Appl. No.: 12/615,085

(22) Filed: Nov. 9, 2009

(65) Prior Publication Data

US 2010/0134605 A1 Jun. 3, 2010

Related U.S. Application Data

(63) Continuation-in-part of application No. 11/292,406, filed on Nov. 30, 2005, now Pat. No. 7,945,077.

(60) Provisional application No. 61/112,509, filed on Nov. 7, 2008.

(51) Int. Cl.
*G06K 9/00* (2006.01)

(52) U.S. Cl. .......................................... 382/128; 356/51

(58) Field of Classification Search .................. 382/128; 356/51; 600/473
See application file for complete search history.

(56) References Cited

U.S. PATENT DOCUMENTS

| | | | | |
|---|---|---|---|---|
| 5,782,770 | A | 7/1998 | Mooradian et al. | |
| 5,986,770 | A | 11/1999 | Hein et al. | |
| 6,507,747 | B1 | 1/2003 | Gowda et al. | |
| 6,529,769 | B2 | 3/2003 | Zigler | |
| 6,989,140 | B2 * | 1/2006 | Tidmarsh et al. | 424/9.1 |
| 7,145,645 | B2 * | 12/2006 | Blumenfeld et al. | 356/73 |
| 7,149,567 | B2 | 12/2006 | Demos et al. | |
| 7,792,570 | B2 * | 9/2010 | DiMarzio et al. | 600/476 |
| 7,821,698 | B2 * | 10/2010 | Zeng et al. | 359/285 |
| 8,088,839 | B2 * | 1/2012 | Kumacheva | 523/204 |
| 2002/0049386 | A1 | 4/2002 | Yang et al. | |
| 2002/0065468 | A1 | 5/2002 | Utzinger et al. | |
| 2002/0103439 | A1 | 8/2002 | Zeng et al. | |
| 2004/0006275 | A1 | 1/2004 | Demos et al. | |
| 2005/0218338 | A1 | 10/2005 | Wulf et al. | |
| 2008/0194969 | A1 | 8/2008 | Werahera et al. | |

OTHER PUBLICATIONS

Alfano, R.R. et al., "Laser induced fluorescence spectroscopy from native cancerous and normal tissues", IEEE J. Quantum Electron., 20, 1984, pp. 1507-1511.
Kapadia, C.R. et al., "Laser-induced fluorescence spectroscopy of human colonic mucosa detection of adenomatous transformation", Gastroenterology, 99, 1990, pp. 150-157.
Kortum, R.R., et al., "Spectroscopic diagnosis of colonic dysphasia", Photochem & Photobio., 53, 1991, pp. 777-786.
Frank, C.J., et al., "Characterization of human breast specimens with Near-IR Raman spectroscopy", Anal Chem., 66, 1994, pp. 319-326.

(Continued)

*Primary Examiner* — John Strege
(74) *Attorney, Agent, or Firm* — John P. Wooldridge

(57) ABSTRACT

In vivo endoscopic methods an apparatuses for implementation of fluorescence and autofluorescence microscopy, with and without the use of exogenous agents, effectively (with resolution sufficient to image nuclei) visualize and categorize various abnormal tissue forms.

27 Claims, 9 Drawing Sheets

OTHER PUBLICATIONS

Ramanujam, N., et al., "Cervical precancer detection using a multivariate statistical algorithm based on laser-induced fluorescence spectra at multiple excitation wavelengths", Photochemistry and Photobiology, 64, 1996, pp. 720-735.

Backman, V., et al., "Detection of preinvasive cancer cells", Nature, 406, 2000, pp. 35-36.

Hsing-Wen, W., et al., "Quantitative laser scanning confocal autofluorescence microscopy of normal, premalignant, and malignant colonic tissue", IEEE Tranactions on Biom. Engineering, 46, 1999, 101246-52.

Pavlova, I., et al., "Microanatomical and biochemical origins of normal and precancerous cervical autofluorescence using laser-scanning fluorescence confocal microscopy", 77, 2003, pp. 550-555.

Huang: Z.W., et al., "Laser-induced autofluorescence microscopy of normal and tumor human colonic tissue", Int. J. of Oncology, 24, 2004, pp. 59-63.

Rajadhyaksha, M., et al., "Confocal examination of nonmelanoma cancers in thick skin excisions to potentially guide Mohs micrographic surgery without frozen histopathology", J. of Investigative Dermatology, 117, 2001, pp. 1137-1143.

Gannaway, J. N., et al., "Second harmonic imaging in the scanning optical microscope", Optical and Quantum Electronics, 10, 1978, pp. 435-439.

Denk, W. et al., "Two-photon Laser scanning fluorescence microscopy", Science, 248, 1990, pp. 73-76.

Zumbusch, A., et al., "Three-dimensional vibrational imaging by coherent anti-Stokes Raman scattering", Phys. Rev. Lett., 82, 1999, pp. 4142-4145.

Demos, S.G., et al., "Hyperspectral Imaging of Cells: Towards Real-Time pathological Assessment", Proc. of SPIE, vol. 5201, pp. 133-137, 2003.

* cited by examiner

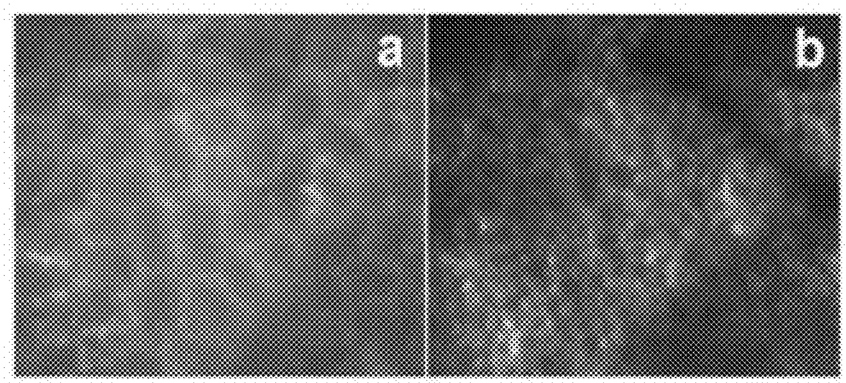
Figure 1a Figure 1b
Figure 2a Figure 2b
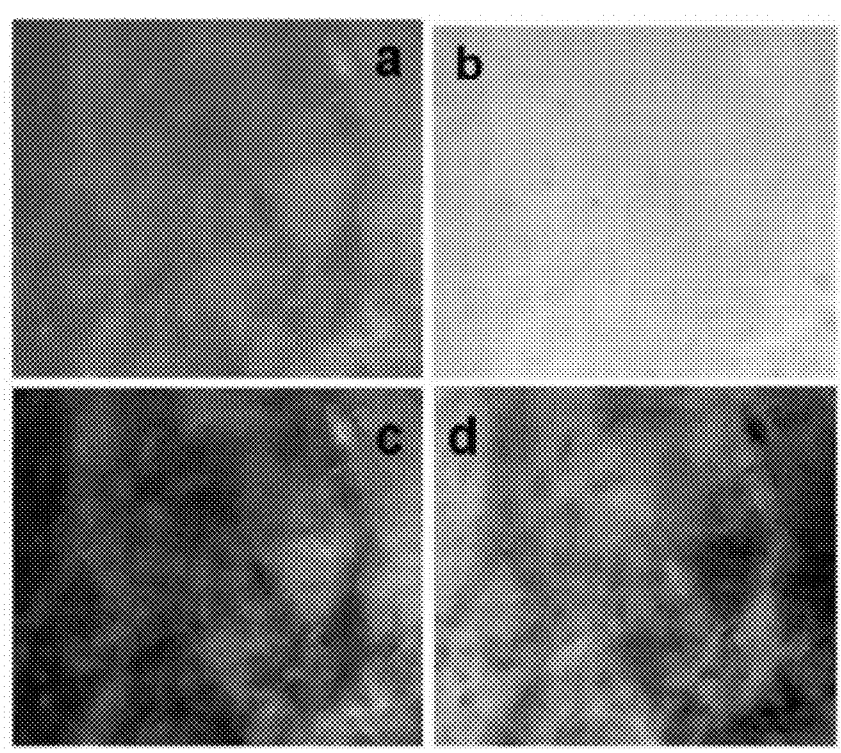
Figure 2c Figure 2d

Figure 3a Figure 3b Figure 3c
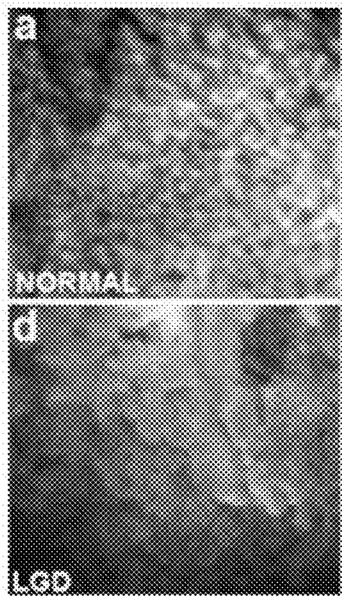
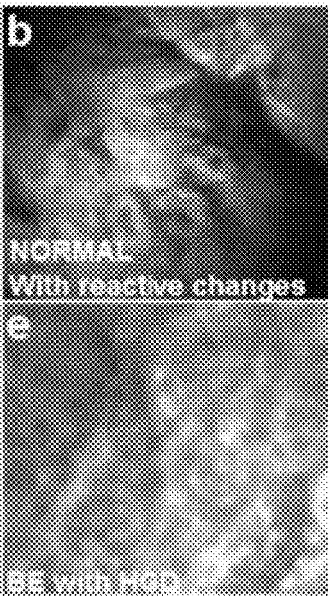
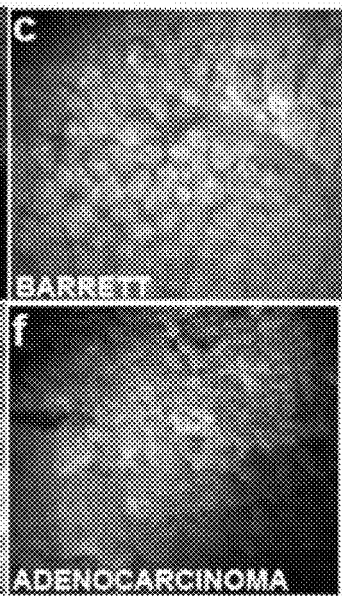
Figure 3d Figure 3e Figure 3f
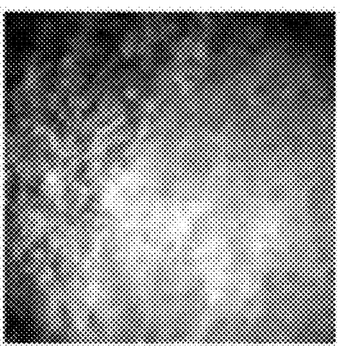
Figure 4

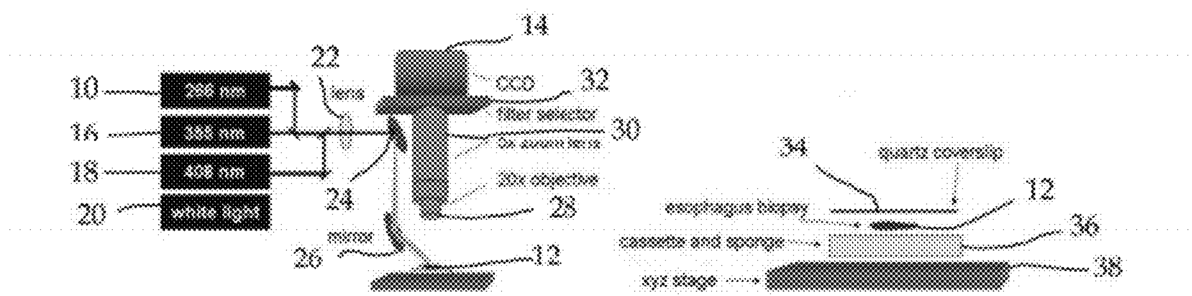
Figure 7a
Figure 7b
Figure 8a
Figure 8b
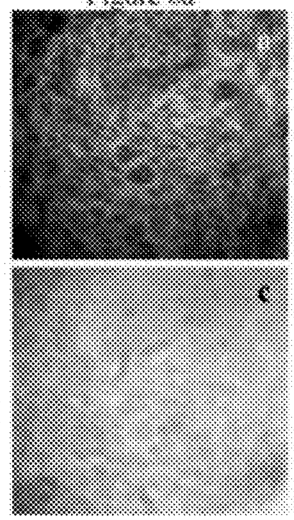
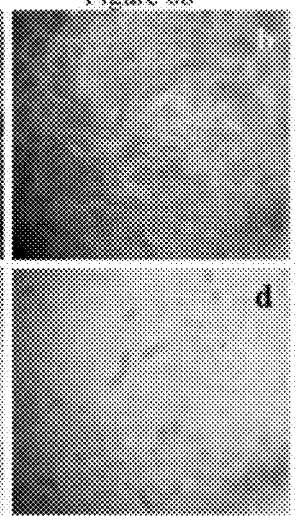
Figure 8c
Figure 8d

IN VIVO SPECTRAL MICRO-IMAGING OF TISSUE

This application claims priority to U.S. Provisional No. 61/112,509, filed Nov. 7, 2008. This is a continuation-in-part of U.S. application No. 11/292,406, filed Nov. 30, 2005 now U.S. Pat. No. 7,945,077, incorporated herein by reference.

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to medical diagnostics for tissue investigation and more particularly, it relates instruments for real-time monitoring of tissues in vivo.

2. Description of Related Art

Esophageal adenocarcinoma will claim approximately 89.6% of all cases within 5 years of diagnosis [2,3]. This rare but fatal disease has been increasing in the United States at the alarming rate of approximately 2% every year, and has been linked to conditions such as obesity [3-7]. A significant factor of the poor prognosis is the difficulty of early detection when disease initiates in the epithelial tissues before becoming invasive. The epithelial layer may contain intestinal metaplasia (Barrett's esophagus), low-grade dysplasia, high-grade dysplasia, and/or carcinoma in heterogeneous (initiation) sites. Additionally, onset is often asymptomatic until the disease has advanced to the point where the curative therapy may be unavailable. This asymptomatic, and potentially heterogeneous nature of diseased esophageal mucosa makes early detection of abnormal progression almost impossible to distinguish using current endoscopic surveillance of the esophagus [8]. Esophageal surveillance is presently done using standard white light video endoscopy (SVE) and/or chromoendoscopy, the use of contrast agents such as acetic acid or methylene blue [9]. Current SVE procedures rely on visual assessment of the tissue mucosa followed by random 4 quadrant biopsy of suspicious epithelial tissue [8-11]. Often times, dysplastic progression is invisible to SVE due to low resolution, and missed during random sampling. This random sampling is of great concern due to the inherent sampling error and delayed turn-around time for results [12]. The excised tissue is preserved and prepared for histologic evaluation of microstructure change; however, discrepancies in histopathology readings prompted a modification of standard esophageal classification [13]. Presently, a large amount of research is being exerted in the optical field to develop early detection screening systems for these premalignant conditions.

Fluorescence optical spectroscopy under ultra violet (UV) light has been shown to provide a powerful method for minimally invasive detection of biochemical and morphological changes [14-16] in regions of the gastrointestinal (GI) tract [11,17,18]. While spectroscopy is very sensitive in detecting these changes, the point measurements are averaged over an area and do not provide a comprehensive image. Diagnostic information would be better relayed and more familiar to the surgical team as an image. Time resolved imaging techniques such as time correlated single photon counting (TCSPC) and fluorescence lifetime imaging (FLIM)) have been explored [19]. Investigators acknowledged the difficulties in fitting multiple exponentials to resulting data, as well as achieving the required resolution with these techniques.

Optical coherence tomography (OCT) provides images of major structural components of the mucosa and submucosa, including esophageal glands, intestinal villi, colonic crypts and blood vessels, at higher resolution than catheter probe endoscopic ultrasound (CPEUS) [20]. While these features allow visibility of normal squamous mucosa and specialized intestinal metaplasia in the esophagus, OCT has not yet been shown to adequately differentiate between dysplastic and intramucosal carcinoma [21].

Magnification high-resolution endoscopy is commercially available from Olympus [22-24]. This wide-field zoom endoscope system provides images of mucosal and vascular patterns by implementing white light (WL), autofluorescence (AF), and/or narrowband imaging (NBI). Results suggest an increase in lesion detection, although it was not shown to provide cellular imaging.

Confocal microscopy is an optical imaging technique used to increase micrograph contrast and/or to reconstruct three-dimensional images by using a spatial pinhole to eliminate out-of-focus light in specimens that are thicker than the focal plane. This technique has gained popularity in the scientific and industrial communities and typical applications are in life sciences and semiconductor inspection. The principle of confocal imaging was patented by Marvin Minsky in 1957 and aims to overcome some limitations of traditional wide-field fluorescence microscopes. In a conventional (i.e., wide-field) fluorescence microscope, the entire specimen is flooded in light from a light source. In the case of imaging a tissue specimen, the excitation light has an average photon penetration depth that is strongly dependant on wavelength and it is on the order of about 2 mm at 400 nm excitation to more than 1 cm in the near infrared spectrum. The resulting fluorescence arises from all regions of the specimen that are illuminated by the excitation light and subsequently, the depth of the tissue region that produces fluorescence is about equal to the average photon penetration depth of the excitation light. This fluorescence is detected by the microscope's photodetector or camera. However, as the image plane of a conventional microscope has a thickness on the order of 10-50 μm, nearly all the signal collected by the microscope's optics is out of focus, thus not contributing to the formation of an image but act as background signal and is equivalent to a background noise. This problem is further enhanced by multiple scattering of the photons arriving from deeper tissue layers resulting in a loss of the image information. In contrast, the confocal microscope eliminated this "background signal" by using point illumination and a pinhole in an optically conjugate plane in front of the detector to eliminate out-of-focus information—the name "confocal" stems from this configuration. As only fluorescence very close to the focal plane can be detected, the image contrast, particularly in the sample depth direction, is much better than that of wide-field microscopes. However, due to the fact that much of the light from sample fluorescence is blocked at the pinhole, this increased resolution is at the cost of decreased signal intensity, and is more time intensive as it requires image formation via point-by-point scanning. The long exposure time effectively eliminates most, in not all, in vivo uses when tissue autofluorescence is used as the primary signal for image formation, due to the fact that living tissue is always moving to some degree. In addition, the ability of an operator to keep a microscope system to a still (no motion) position is also limited and practically impossible when microscopic resolution is needed. Furthermore, for in-vivo application, the scanning speed for image acquisition directly determines how large an area within the region of interest (such as esophagus) can be examined with the microscope because the time available in the OR is limited and very expensive. Pentax Corporation and Mauna Kea Technologies both commercially distribute a confocal endomicroscope system [25,26]. While in vivo cellular imaging was achieved, the use of fluorescein was required for both. The results are thus dependent on fluorescein uptake, concentration, leakage, pattern distortion, and other complications. Additionally, it was noted that encasement of the individual white light and confocal optics at the distal end of the endoscope limited the ability of the white light image to guide placement of the confocal collection point [26].

Confocal microscopy has been utilized to characterize tissue autofluorescence of frozen esophageal biopsies [27]. While histopathologically comparable images were obtained from the sectioned and stained samples, the destructive nature in preparing the sample eliminates this approach from in vivo application. Confocal techniques have also been implemented in a dual axes configuration to image fresh tissue [28,29]. The first prototype used acetic acid and was shown to provide ex vivo images of glandular crypt size and organization, although nuclei were not specified to be distinguishable. The second prototype used fluorescein to obtain in vivo images of blood vessels, but suffered from leakage over time and did not provide cellular images. The advancement toward endoscopic implementation of microscopy is understood to be a key towards endoluminal visualization.

Endoscopic confocal [30], or endoscopic wide-field [31] microscopy implement fluorescein and acriflavine hydrochloride contrast agents respectively. While visualization of the nuclei is critical for diagnosis, contrast enhancement using exogenous agents raise concerns about allergic reactions, non-specific binding, saturation [8], dosage and toxicity levels, or delay due to chemical synthesis, manufacture, or processing [32].

Backscattered second harmonic generation and two-photon AF microscopy have been used to image the esophagus using near infrared (NIR) wavelengths without the use of contrast agents [33]. In addition to requiring complex nonlinear instrumentation, these methods focus on the esophageal stroma rather than the nuclei.

Accordingly, endoscopic methods for implementation of AF (i.e., without exogenous agents) in vivo microscopy to effectively visualize and categorize various abnormal esophageal tissue forms is understood to be a key towards endoluminal visualization.

SUMMARY OF THE INVENTION

It is an object of the present invention to provide in vivo endoscopic methods for implementation of AF microscopy, without the use of exogenous agents, to effectively (with resolution sufficient to image nuclei) visualize and categorize various abnormal esophageal tissue forms.

Another object is to provide apparatuses capable of in vivo endoscopic methods for implementation of AF (without exogenous agents) microscopy to effectively visualize and categorize various abnormal esophageal tissue forms.

Still another object is to provide UV AF imaging methodologies that clearly show contrast and spatial resolution of 1 μm for distinguishing normal and abnormal esophageal structures at the cellular level based on morphological change.

These and other objects will be apparent based on the disclosure herein.

A microscope system described in US20070160279(A1), incorporated herein by reference, has been used to determine the most effective excitation-emission combinations for imaging changes of structural and biochemical characteristics in esophagus tissue [1]. Ultra violet (UV) wavelengths were implemented in this platform as the excitation sources for ex vivo human esophagus tissue biopsies. The present inventors have made the discovery that imaging of the superficial tissue microstructure can be achieved using conventional wide field autofluorescence microscopy under excitation with UV light of less than 400 nm. Although the exact mechanism is still not completely clear, they hypothesize that this becomes possible via two main mechanisms. The first mechanism now discussed is that the excitation UV light only penetrates tissue to about 100 μm or less and as a result, a sufficient amount of the fluorescence signal produced in the superficial tissue layer can be contained within the thickness of the image plane of the microscope, thus the out of focus signal (background) is sufficiently reduced to allow the formation of high contrast images of tissue microstructure using the native fluorescence (autofluorescence) of the tissue cells and intracellular components. There is no need for a pinhole because substantially all of the AF is produced within this superficial tissue layer that has thickness comparable to the thickness of the image plane. This hypothesis is supported by additional experimental results that the contrast of AF images obtained with excitation wavelengths longer that about 300 nm is lower to that when the excitation wavelength in shorter than about 300 nm, suggesting that the photon penetration depth for shorter UV wavelength is also shorter giving rise to a higher image contrast. The second mechanism now discussed is that there is sufficient variability in the concentration of chromophores (that can be photo-excited with UV light) contained within subcellular and intracellular components so that the microscopic autofluorescence image of the tissue reveals the microstructure and organization of the superficial layer in a similar way to that provided by H&E staining.

Further, since the present invention provides much more light for imaging than the confocal microscope, it is able to produce an autofluorescence image in much less time (~10 microseconds or less). This reduced time required to collect enough light to produce an adequate image enables use of autofluorescence microscopy in vivo. The limit on the duration of the image acquisition window is that the image must be collected in an exposure time in which the target tissue (such as esophagus) and/or instrument (such as micro-endoscope) moves no more that the resolution of the optical system. Thus, if the desired resolution of the optical system is 1 micrometer, then the time it takes the target tissue to move 1 micrometer is the limit of the duration of the image acquisition window. The resolution S is equal to the speed, in not all, that the tissue is moving times the limit on the exposure time. Thus, if S=1 micrometer and the combined speed of motion is on the order of V=5 millimeter/second, then the time duration limit is 200 μsec. This technology does not require exogenous agents and is non-destructive to the sample. The present invention provides a minimally (or non) invasive method to visualize and categorize various abnormal esophageal tissue forms such as Barrett's esophagus (BE), low-grade dysplasia (LGD), high-grade dysplasia (HGD), and adenocarcinoma (ADC) in vivo and in real time. Endoscopic implementations are provided.

The invention herein utilizes the AF optical signal and provides resolution sufficient to image nuclei. This technology thus bypasses the complications of contrast agents while still obtaining diagnostic information sufficient to meet the current Hematoxylin and Eosin (HE) Staining Protocol, which is sometimes referred to in the field as the H&E gold standard. Embodiments of the present invention have been successfully implemented into endoscopes. A prototype zoom video endoscope probe was originally designed to operate in contact mode and is equipped with a white light guide, objective lens, and CCD encased at the tip of the endoscope probe. The probe distal end outer diameter is 3.2 mm and has a 300×300 μm field of view. The design has previously been shown to image cell nuclei with methylene blue contrast enhancement [34-36]. The present invention is able to acquire and categorize AF images of tissue without the use of contrast agents or hardware modification.

BRIEF DESCRIPTION OF THE DRAWINGS

The accompanying drawings, which are incorporated into and form a part of the disclosure, illustrate embodiments of the invention and, together with the description, serve to explain the principles of the invention.

FIGS. 1*a* shows a 245 μm×215 μm image of one leaf under excitation from light at a wavelength of 266 nm.

FIGS. 1*b* shows a 245 μm×215 μm image of one leaf under excitation from light at a wavelength of 355 nm.

FIGS. 2*a-d* show 245 μm×215 μm images of one high grade dysplastic human esophagus biopsy under excitation from light at a wavelength of 266 nm, 355 nm, 266 nm/355 nm and 355 nm/266 nm, respectively.

FIGS. 3*a-f* show 245 μm×215 μm human esophagus images of optical biopsies of normal tissue, normal tissue with reactive changes, Barrett esophagus (BE), low-grade dysplasia (LGD), BE with high-grade dysplasia (HGD) and adenocarcinoma, respectively.

FIG. 4 shows a 350 μm×330 μm image that illustrates a visible difference between normal (lower right) and abnormal (upper left) tissue within the same image.

FIG. 7*a* shows an exemplary autofluorescence microscopy system.

FIG. 7*b* illustrates specimen placement.

FIGS. 8*a*-8*d* are images of a specimen under (a) 266 μnm, (b) 355 nm, and (c) 408 nm laser excitation along with an image acquired using the same set-up under (d) white light illumination.

DETAILED DESCRIPTION OF THE INVENTION

Figure 5:
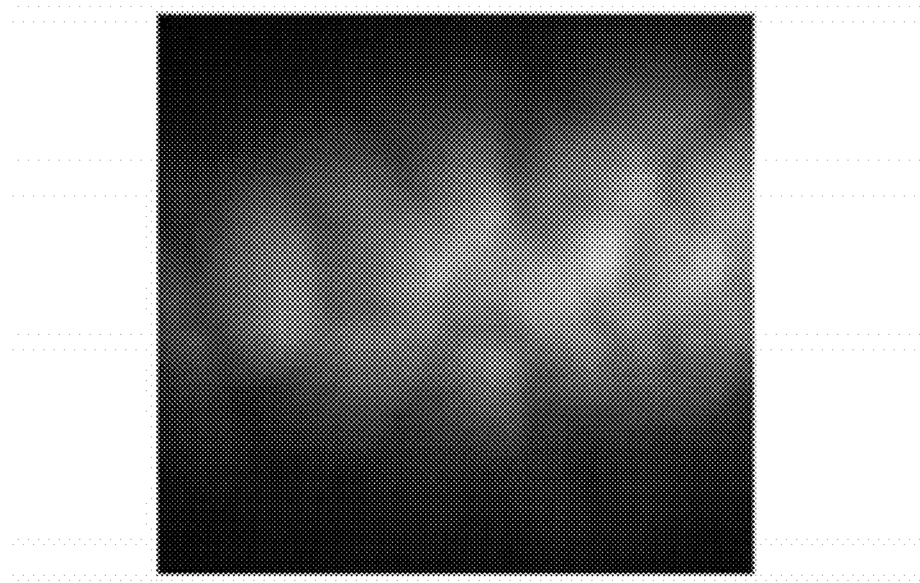
FIG. 5 shows a microscopic image of a rat kidney under excitation at 266 nm revealing tubular structure.

FIG. 1 exemplifies the different 245 μm×215 images acquired, using a prototype microscope, of a single leaf sample under the two specific excitation wavelengths, 266 nm and 355 nm respectively. The prototype microscope system has been built to test the designing principles of this invention. These autofluorescence images demonstrate the different microstructures visible within the leaf under different excitation.

FIGS. 2*a-d* show 245 μm×215 μm images of one high-grade dysplastic human esophagus biopsy under excitation from light at a wavelength of 266 nm, 355 nm, 266 nm/355 nm and 355 nm/266 nm, respectively. Clearly, the abnormal tissue autofluorescence appears different under 266 nm and 355 nm excitation. Image processing was used in the images of FIGS. 2*c* and 2*d* to further enhance contrast.

Images under 266 nm excitation were seen to provide spatial resolution and contrast sufficient to visualize nuclei. FIG. 3 shows examples of human esophagus optical biopsies, confirmed by histological analysis to be a progression of disease from normal squamous mucosa to esophageal adenocarcinoma. Specifically, FIGS. 3*a-d* show 245 μm×215 μm human esophagus images of optical biopsies of normal tissue, normal tissue with reactive changes, Barrett's esophagus (BE), low-grade dysplasia (LGD), BE with high-grade dysplasia (HGD) and adenocarcinoma, respectively. All ex vivo tissue biopsies were placed on a sponge in a standard cassette of plastic non-fluorescing material. The tissue was kept moist with a solution known as Roswell Park Memorial Institute (RPMI) solution and imaged without tissue preparation such as staining or fixation. A quartz slide was placed on top of the sample to produce an even imaging surface and a uniform biopsy thickness of approximately 1 mm. Unless specified, a 400 nm long pass filter was used during every experiment. Each sample was imaged during 2 to 5 second exposure depending on the detected signal intensity. After imaging, the tissue sample was immediately placed in formalin for preservation and returned to the grossing lab for histologic evaluation. Pathology diagnosis was confirmed by at least two experienced gastrointenstinal (GI) pathologists and taken as the gold standard.

The hyperspectral microscope design (describe below) has the additional feature of providing margin delineation. FIG. 4 below illustrates this advantage. Specifically, FIG. 4 shows a 350 μm×330 μm image that illustrates a visible difference between normal (lower right) and abnormal (upper left) tissue within the same image. The benefit of this system is the ability to provide targeted biopsies for immediate imaging of the surrounding areas for adequate sampling.

This UV AF imaging methodology clearly provides the contrast and spatial resolution of 1 μm necessary to distinguish normal and abnormal esophageal structures at the cellular level based on morphological change. The biochemical information embedded within the optical images remains to be extracted and analyzed in order to fully realize the potential of this technique. Methods that best represent the change in autofluorescence intensity due to disease progression are enabled. Optical capabilities and parameters of the current platform prototype are easily implemented into endoscopic embodiments, examples of which are shown below. The present invention applies spectroscopic methods in a microscopic approach to provide real-time in vivo diagnostic information.

The technology is applied to murine kidney tissue as shown in FIG. 5. Specifically, FIG. 5 shows a microscopic image of a rat kidney under excitation at 266 nm revealing tubular structure. The autofluorescence image of tubules is visible under combined 266 nm and 325 nm excitation using an embodiment endoscope compatible probe.

Figure 6:
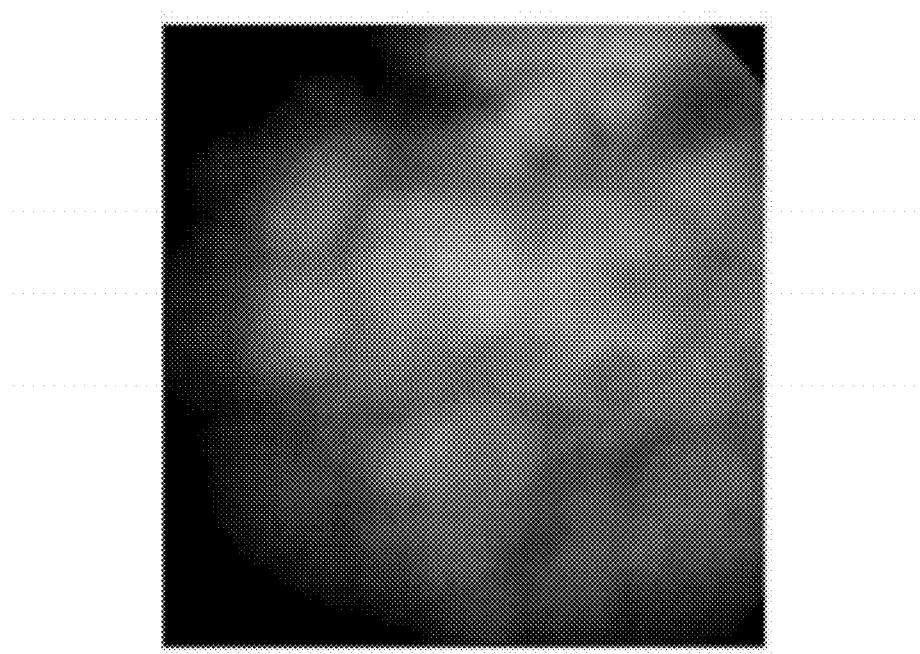
FIG. 6 shows a microscopic image of an ex vivo human esophagus biopsy image under 325 nm excitation showing abnormal structure.

FIG. 6 shows a microscopic image of an ex vivo human esophagus biopsy image under 325 nm excitation showing abnormal structure.

A study utilizing a prototype of the present invention was conducted in accordance with an institutional review board (IRB) approved protocol at the University of California, Davis Medical Center. The preliminary results reported herein represent the findings from an initial population of 30 patients with a history of Barrett's esophagus.

After obtaining informed consent from patients undergoing routine surveillance for Barrett's esophagus, standard forceps were used during endoscopy to obtain one biopsy specimen from the vicinity of the squamocolumnar junction, and two specimens from the gastroesophageal junction for a total of three biopsy specimens per patient. Each specimen was immediately placed in an individually labeled container with RPMI1640 media and transported to the imaging lab located in the same building where the AF microscopy measurements were taken. All specimens were imaged using standard handling. At least three AF images were recorded from specimens that presented high microstructure uniformity (typically observed in normal tissue). Additional images were recorded when tissue images presented altered or changing morphology to best capture these variations. Each image covers a field of view of 670×650 $\mu m^2$ of the surface of the tissue sample. After imaging, each tissue biopsy specimen was immediately placed in 10% formalin for fixation and transferred to pathology for tissue diagnosis. The pathological evaluation was confirmed by at least two expert pathologists and taken as the diagnostic gold standard from which the optical images were categorized. Direct correlation between optical images and histological stain of the same tissue was not possible in this study because the autofluorescence images were acquired along the epithelial/luminal plane, while the histological stained tissue is examined from the plane orthogonal to the surface. Since these biopsy specimens were used for clinical diagnosis, it was not possible to employ an alternate processing technique (slicing from the surface plane).

Each individual biopsy specimen was positioned at the center of a sponge in a standard pathology specimen cassette, which was placed on a xyz translation stage. Ex vivo specimens were imaged without any tissue preparation with the prototype microscope-imaging platform.

FIGS. 7*a* and 7*b* illustrate the experimental arrangement for the imaging of the esophagus tissue specimens used in this study. Specifically, FIG. 7*a* is a schematic depicting the autofluorescence microscopy system. A compact diode-pumped solid state laser 10 operating at 266 nm was the main light source used to excite the sample 12 and generate the flourescense and/or autoflourescense images, which were recorded using a liquid nitrogen cooled charge coupled device 14. Additional compact lasers 16 and 18 operating at 355 nm and 405 nm, respectively, shown in FIG. 7*a*, were used in the preliminary phase of the study that was focused on determining the optimal excitation wavelength. A white light source 20 is also depicted. The figure also shows a lens 22 and two mirrors 24 and 26 for directing light from the sources onto sample 12. The collection optics include a 20× objective 28, a 5× soom lens 30, a filter selector 32 and the CCD 14. FIG. 7*b* illustrates specimen (sample 12) placement. The sample 12 is held between a quartz coverslip 34 and a cassette (and sponge) 36, which located on an xyz stage 38.

FIGS. 8*a*-8*d* are images of a specimen under (a) 266 nm, (b) 355 nm, and (c) 408 nm laser excitation along with an image acquired using the same set-up under (d) white light illumination. The contrast in these images was linearly adjusted to qualitatively optimize visualization of the tissue microstructure. The features observed in the white light illumination image (FIG. 8*d*) were due to artifacts arising from dust on the optical elements. These artifacts are also visible in the AF images under 355 nm and 408 nm excitation, but not under 266 nm excitation. The images acquired under excitation at 266 nm provided the highest image contrast. For this reason, attention in the analysis of the experimental results obtained under 266 nm excitation.

The images under 266 nm excitation were acquired using a 5 second exposure time with an approximate dose of 30 $mJ/cm^2$. This yielded images with a digitized intensity of about 5000 counts per pixel. It must be noted that high quality images under these excitation conditions were possible with exposure times shorter than one second (or images with digitized intensity of about 500 counts per pixel or higher), but this exposure time was chosen in order to optimize image quality. The optical elements used in the microscope were not transmitting UV light, thus the images acquired were based on emission in the visible range. To better quantify the spectral range used for imaging, a 400 nm long pass filter was positioned in front of the CCD. Consequently, the experimental method and results can be translated into microendoscope systems, which, until now were currently capable of imaging only in the visible spectral range.

Figure 9A:
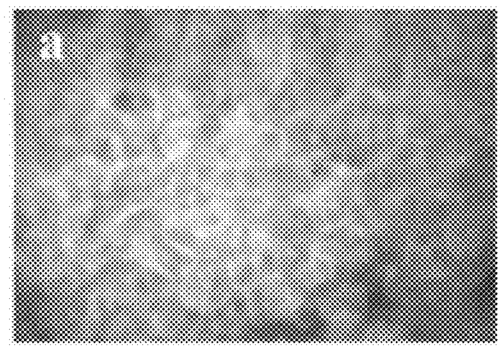
FIG. 9*a* shows an autofluorescence image under 266 nm excitation of a 434 μm×301 μm section of human esophagus of squamous mucosa.
Figure 9B:
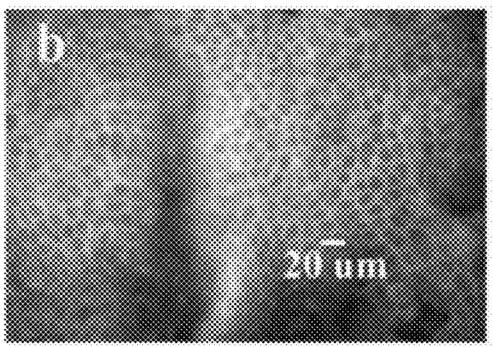
FIG. 9*b* shows an autofluorescence image under 266 nm excitation of a 434 μm×301 μm section of human esophagus of glandular mucosa.
Figure 10A:
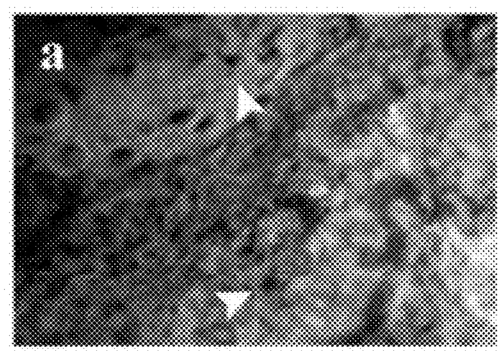
FIG. 10*a* shows an autofluorescence image under 266 nm excitation of human Barrett's esophagus.
Figure 10B:
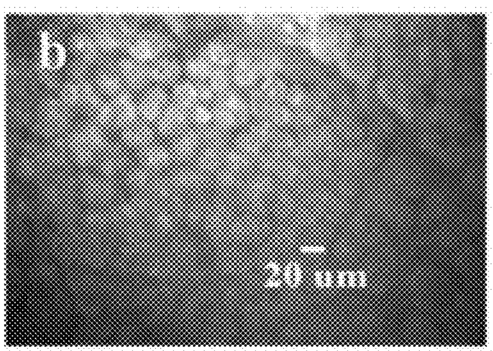
FIG. 10*b* shows an autofluorescence image under 266 nm excitation of human dysplastic glandular epithelium.
Figure 11A:
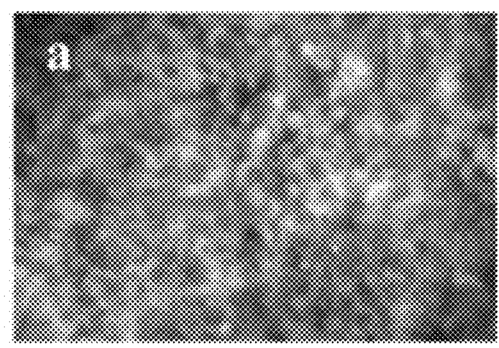
FIG. 11*a* shows an image of high-grade dysplasia.
Figure 11B:
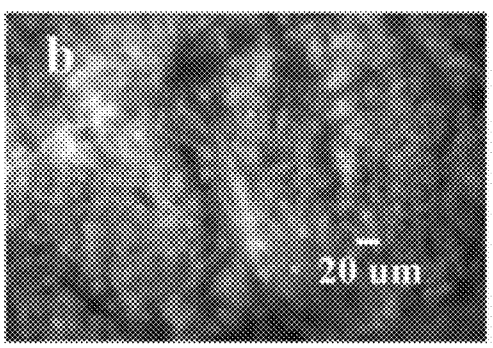
FIG. 11*b* shows an image of adenocarcinoma.

Typical AF images under 266 nm excitation illustrating the observed epithelial morphology associated with various stages of esophageal disease progression are shown in FIGS. 9*a* and 9*b*. The images shown were selected as representative of distinct classifications based on the opinion of the expert pathologist. Specifically, FIG. 9*a* shows an autofluorescence image under 266 nm excitation of a 434 μm×301 μm section of human esophagus of squamous mucosa, and FIG. 9*b* shows an autofluorescence image under 266 nm excitation of a 434 μm×301 μm section of human esophagus of glandular mucosa. AF images of Barrett's esophagus segments are shown in FIG. 10*a* and FIG. 10*b*. Specifically, FIG. 10*a* shows an autofluorescence image under 266 nm excitation of human Barrett's esophagus and FIG. 10*b* shows an autofluorescence image under 266 nm excitation of human dysplastic glandular epithelium. In FIG. 10*a*, arrows designate what could be goblet cells. High-grade dysplasia is shown in FIG. 11*a*, while FIG. 11*b* shows an adenocarcinoma specimen. These images demonstrated visualization of microstructure morphology that could not be attained during a routine endoscopy. Comparing these AF images with histopathology is a crucial step in establishing the foundation necessary for assessing tissue status in vivo. Specifically, the present inventors wanted to explore the possibility that information needed for the evaluation of cell organization and morphology can be attained from images such as shown in FIGS. 9*a*-11*b*.

The image of normal stratified squamous mucosa of the esophagus in FIG. 9*a*, shows a characteristic tile-like appearance of squamous cells with well demarcated edges at the periphery, probably corresponding to intercellular junctions. The image shown in FIG. 9*b* is from a biopsy specimen collected near the squamocolumnar junction and indicates regular rounded cells with a "honey-comb" appearance of normal glandular mucosa, characteristic of simple columnar epithelium.

FIG. 10*a* demonstrates an AF image of a Barrett's esophagus specimen from non-nodular distal esophageal mucosa. This image exhibits a similar appearance to that of normal glandular epithelium. However, the darker features indicated by arrows may represent goblet cells. This suggested that Barrett's esophagus could potentially be identified among the glandular distal esophageal epithelium, a capability not yet available to endoscopists prior to the present invention. Another example of diseased tissue that appeared normal during endoscopic examination is shown in FIG. 10*b*. This image was taken of a patient biopsy specimen whose pathology revealed dysplasia. The dysplasia was noted to be focal and high-grade rather than low-grade.

FIG. 11*a* illustrates the image of a specimen taken from a patient with high-grade dysplasia and suspicion for adenocarcinoma, reflecting the variation of optical images in relation to the grade of dysplasia and its heterogeneity. Microstructure distortion and change of epithelial morphology was obvious. Early onset of these micro-changes is generally invisible during standard endoscopy and remains undetected until the diseased tissue has reached a symptomatic stage of adenocarcinoma, as illustrated in FIG. 10*b*. This biopsy specimen was obtained from the central portion of a visible tumor approximately 5 cm in length. FIGS. 10*a* and 10*b* share similar deviations from normal glandular epithelial cellular structure. Both specimen images demonstrate a loss of the specific cellular patterns that characterize normal glandular epithelium.

High-grade dysplasia was difficult to identify immediately in FIG. 11*a*, in part due to the suspicion that this specimen also contained adenocarcinoma. Adenocarcinoma, shown in FIG. 10*b*, has a three-dimensional villiform pattern, visibly different from the surface layer of normal glandular cells. Pathological evaluation relies on a cross-sectional view of the biopsies to identify features such as nuclear and cellular disorganizations and basement polarity that indicate dysplastic and malignant activity. However, FIGS. 9*a* through 11*b* demonstrate that there are clear changes in the cellular contour and organization patterns from normal to adenocarcinoma epithelium that can be appreciated with AF microscopy.

The imaging approach discussed herein enables real-time acquisition and display of images depicting the microstructure of the epithelial layer, which can provide diagnostic information. All human esophagus specimens discussed herein were unprocessed and unstained, and the images were acquired shortly after the biopsies were obtained in the operating room. Eliminating the need to prepare the tissue area to be imaged represents a major comparative advantage of this approach. This method, especially when implemented in vivo, provides endoscopists with images of cellular morphology to assist in identifying early disease progression of the esophagus. These critical microscopic changes are invisible under currently used standard endoscopes.

AF emission spectra from various tissue types under UV excitation wavelengths shorter than about 300 nm have been previously investigated. These results suggested that the emission profiles were similar to that of tryptophan, displaying a peak around 330 nm and a smooth tail extending beyond 400 nm.

The results clearly demonstrate that the superficial photon propagation at 266 nm excitation provides imaging of cellular morphology of the epithelial layer. The present invention matches or exceeds the performance of other emerging photonic techniques aimed at providing visualization of tissue microstructure in real-time. For example, FIG. 9*a* presents the superficial layer of squamous cells with visible nuclei that appear to be bright, although nuclei in the subsequent images appear to be dark. This discrepancy may be due to the nature of the stratified epithelia. As the basement layers gradually move toward the lumen of the esophagus, they lose their cuboidal shape for a more squamous surface. The nucleus flattens and undergoes pyknosis (densification) during later stages of maturation. As part of maturation, the nuclei are small and many cells have no nuclei. Imaging cells without nuclei, apoptotic cells, pyknotic nuclei, or the lamina propria surface may produce variable optical results. Nuclei are not clearly visible in the columnar epithelium of FIG. 9*b*, probably due to small size and basal location along the basement membrane. Despite this, squamous and glandular mucosa characteristics are easily recognized in the optical images even by a non-expert.

While squamous and columnar epithelia are clearly outlined in FIGS. 9*a* and 9*b*, it is a greater challenge to identify glandular mucosa from specialized intestinal metaplasia, such as the example in FIG. 10*a*. This image contains visible microstructures that are believed to be goblet cells, a defining characteristic of Barrett's esophagus that is not visible without microscopic capabilities. Dysplastic tissue also cannot be ascertained during routine endoscopic surveillance. Microscopic changes associated with dysplasia were seen in FIG. 10*b*. This biopsy specimen was collected from a patient who underwent esophagectomy that showed extensive high-grade dysplasia without invasion. The nodular appearance of the AF image most likely corresponds to the polypoid dysplastic epithelium.

Figure 12:
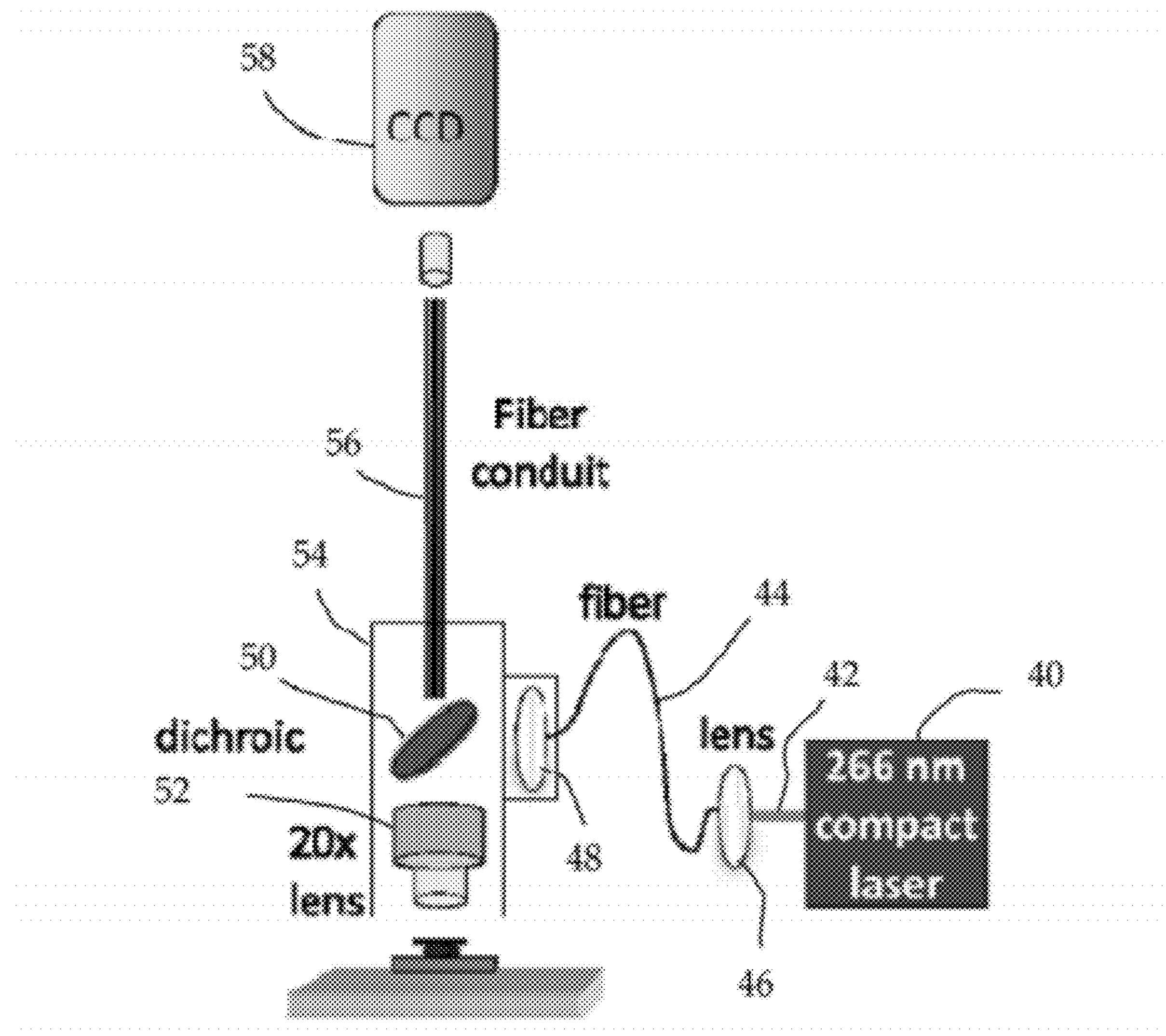
FIGS. 12 through 15 show embodiments of the present invention incorporated into endoscopes.
Figure 13:
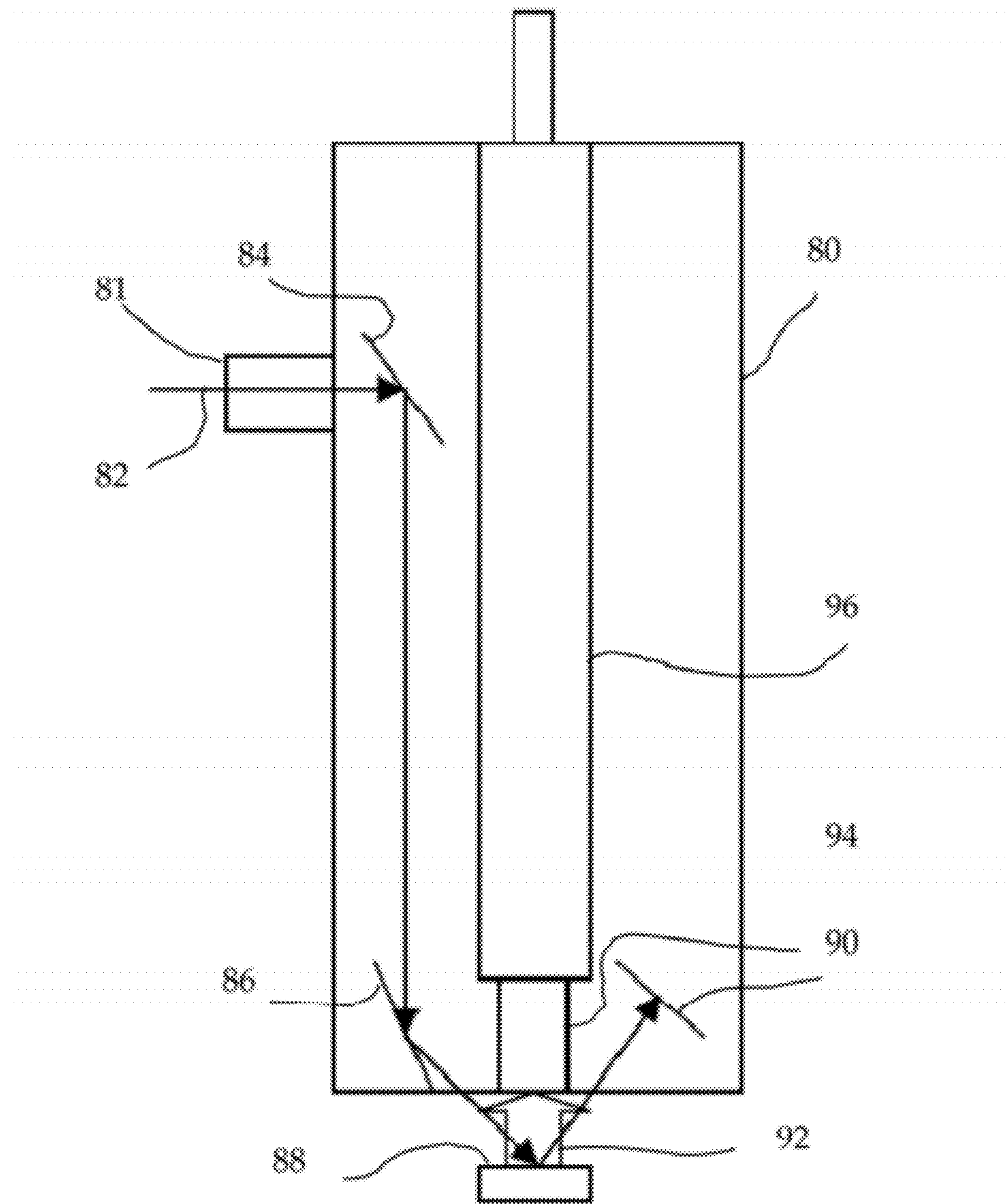
Figure 14:
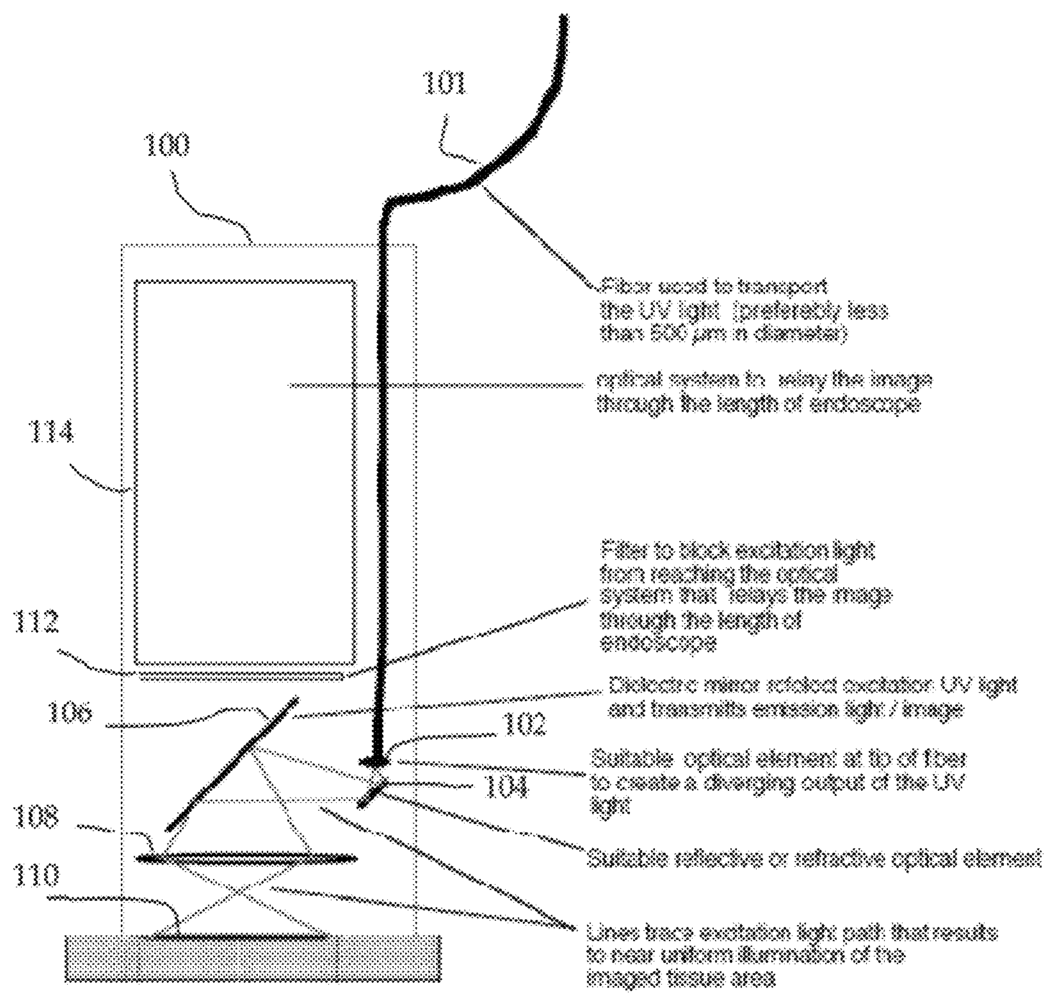
Figure 15:
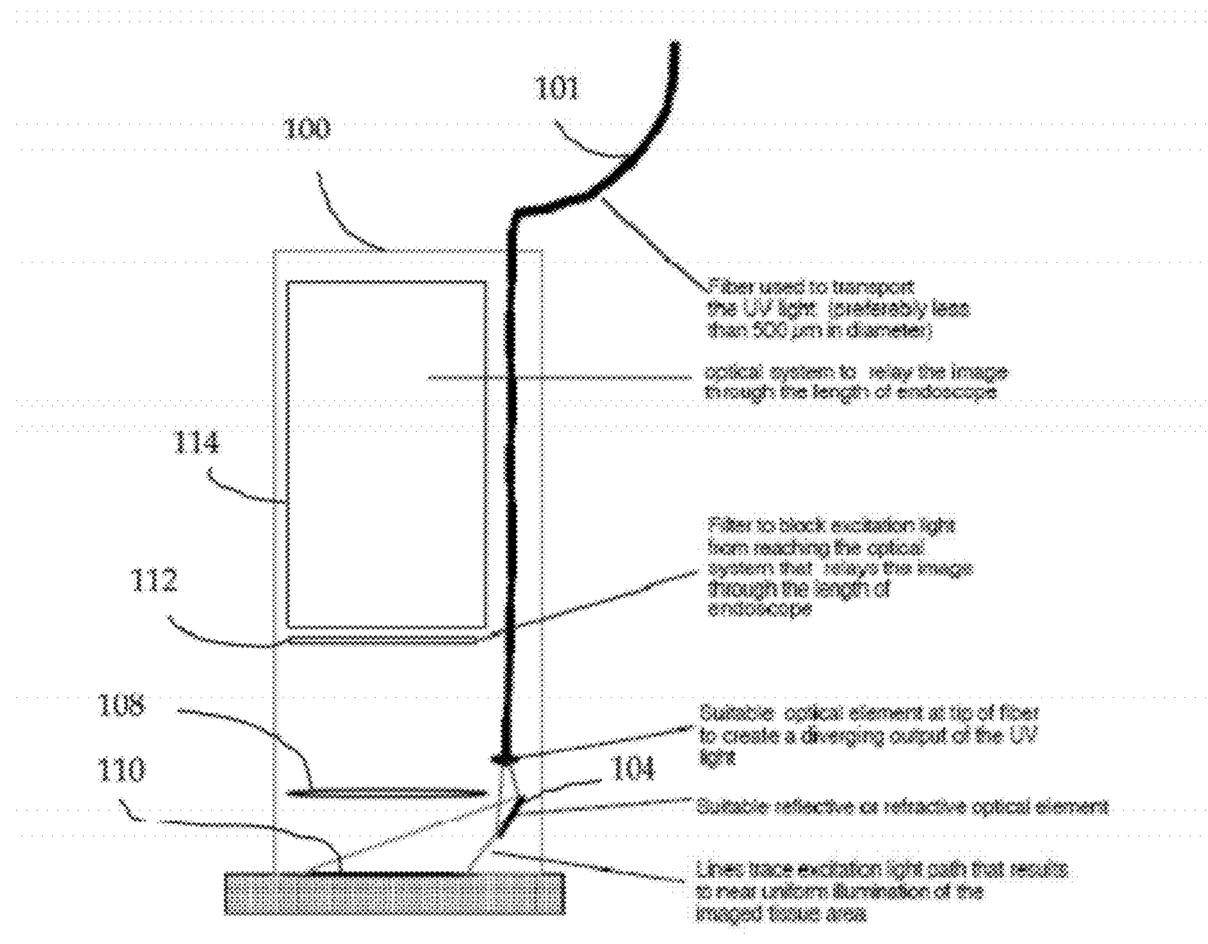

The challenge in standard pathology and likely with AF microscopy is to differentiate low-grade from high grade dysplasia of the esophagus, particularly in view of the well recognized variation of inter-observer and intra-observer reproducibility. Difficulty of microstructure recognition is compounded by the heterogeneous nature of esophageal adenocarcinoma. Barrett's esophagus and adenocarcinoma may be present with or without low- or high-grade dysplasia, increasing the variability of results obtained from the same patient. However, independent of this variability, an optical image using the method discussed in this work is always attainable and may be used to extract diagnostic information when the rules of interpretation to be developed are validated. Dysplastic epithelium, seen in FIGS. 10*b* through 11*b*, illustrate altered organizational and morphological characteristics of tissue at the microscopic level. These images may be considered as offering a projection of increasingly 3-dimensional cells on the 2-dimensional imaging plane, as opposed to the characteristically flattened 2-dimensional surface of squamous and columnar epithelia in FIGS. 9*a*-10*a*. The 3-dimensional progression and heterogeneity of tissue morphology associated with disease compounds the difficulty in focusing a single plane by adding an additional variable to the imaging process. The present inventors' data is based upon correlating the pathological findings with the AF images of the same specimen. Interpretation of the AF images in normal tissue has relatively higher accuracy and precision in view of the uniformity of cell type, compared to tissues with different cell types. (squamocolumnar junction, goblet cells and various grades of dysplasia) which will need more extensive review and correlation of optical images with the pathology. The present invention has enabled the development of rules of interpretation to enable or assist the utilization of the diagnostic information embedded in the optical images in real-time by the endoscopist. FIGS. 12 through 15 show embodiments of the present invention incorporated into endoscopes. FIG. 12 shows a 266 nm laser light source 40 that produces a beam 42 which is coupled with a lens 44 into a fiber optic 46 the output of which is directed by lens 48 toward a dichroic optic 50 which has a coating that reflects the light at 266 nm and transmits the light (flourescense and/or autoflourescense). The 266 nm light that is reflected from dichroic mirror 50 is condensed by a 20× lens 52 onto the sample, which is depicted as in FIG. 7*b*. Note, however, the system is contained within endoscope 54, suitable for in vivo uses. Substantially all of the light that is generated at the sample and directed towards the lens 52 is collected by lens 52 which directs the light through the dichroic 50 and into fiber conduit 56 which propagates the light to the CCD camera 58. FIG. 13 shows an endoscope 80 that provides a port 81 for illumination light 82 which is reflected by a first mirror 84, a second mirror 86, and then onto the target 88 at an angle such that the propagation of illumination light 82 is terminated at beam stop 90. The light 92 generated at and/or in target 88 that is directed towards collection optic 94 is substantially collected thereby and is then directed through a light conduit 96 into a suitable detection and imaging system. The angle at which mirror 86 directs light 82 onto target 88 is large enough the substantially none of the light 82 is collected by collection optic 94. The endoscopic 100 shown is FIG. 14 provides a fiber 101 (in one case having a diameter of 500 μm or less) to transport the UV illumination light to a suitable optical element 102 such as a lens, which produces a diverging beam that is reflected by a first reflector 104 and then by a dichroic optic 106 through lens 108 and onto target 110. The flourescense and/or autoflourescense that is produced at and/or in the target 110 that is directed towards lens 108 is substantially collected by lens 108 and propagates through dichroic optic 106, and then through a filter 112 that is selected to block the illumination light from the optical system 114 that relays the flourescense and/or autoflourescense to a suitable detection and imaging system. FIG. 16 shows a similar endoscope as in FIG. 14, without the second mirror and dichroic and where the sole mirror 104 is positioned to reflect the illumination light at an angle onto the target, in a manner similar to the embodiment of FIG. 13. Filter 112 is optionally used in this embodiment due to the angular delivery of the illumination light.

Obtaining diagnostic information in real-time without contrast agents, sample preparation, time intensive, or prohibitively expensive and complicated instrumentation may be necessary for acceptance of such technology by the medical community and the health care system. This AF method has been implemented for the examination of freshly excised tissue before pathology diagnosis. In this case, UV exposure will not be an issue since low intensity avoids compromise of the tissue sample. While the proof of principle work has lead to in vivo microscopic AF imaging of tissue via endoscopy, the use of laser excitation, particularly in the UV, requires a design that minimizes exposure and optimizes signal throughput. The AF images presented herein were acquired under an approximate dose of 30 mJ/cm$^2$ but images acquired with one tenth of that exposure were of reasonably high quality. In addition, the AF images were collected using a 400 nm long pass filter, thus rejecting most of the emission signal under 266 nm excitation. Moreover, the CCD detector was not optimized for highest sensitivity in this spectral region (400-500 nm). Therefore, a system designed with similar optical parameters but optimized for signal detection easily meets the maximum permissible exposure (MPE) designated ANSI standard for exposure to UV wavelengths between 180 nm-302 nm of 3 mJ/cm$^2$. The present, in vivo AF microscopy method provides information for disease diagnosis that helps detect esophageal disease at an earlier stage. The same technique is suitable for application in other tissue systems. In the case of the current gold standard, stained tissue sections are imaged and interpreted using standard methods that have been developed to assist diagnosis such as the Vienna classification system. The Vienna classification is a standard used with the exception of category 4.2 noninvasive carcinoma (carcinoma in situ). Diagnosis of disease with AF microscopy might require the development of analogous rules, examples of which are provided herein.

The present inventions capability of UV AF imaging of targeted sites in vivo at dimensions as small as 1 μm enable new methodologies for diagnosing abnormal tissue. Such methodologies include (i) not taking a sample of any pavement-like, scaly pattern of normal squamous esophageal cells, with well defined cell-to-cell junction, (ii) taking a sample of any normal columnar mucosa having a honeycomb like pattern with goblet cells for diagnosis of Barrett's esophagus, (iii) not taking a sample of any normal columnar mucosa if known to be Barrett's esophagus and only dysplasia is of concern, (iv) taking a sample of a glandular crypt which appears as one or more depressions or large dark holes on the surface of columnar epithelium, (v) taking a sample of dysplastic epithelium where the surface is thrown into multiple papillary, villiform or cauliform structures, (vi) taking a sample of disorganized tissue with loss of the specific cellular outline patterns characteristic of normal squamous or columnar epithelia and/or (vii) taking a sample of epithelial mucosa with abnormal blood vascular pattern or angiogenesis associated with malignant neoplasia. These steps may be performed singly or in any number and combination. Other steps for diagnosing abnormal tissue will be apparent to those skilled in the art and such are within the scope of the present invention.

References (Incorporated Herein by Reference)

U.S. Provisional No. 61/112,509, filed Nov. 7, 2009 is incorporated herein by reference. U.S. Pat. No. 7,587,236 is incorporated herein by reference.

1. Demos, S. G., et al. "Imaging of tissue microstructures using a multimodal microscope design." IEEE Journal of Selected Topics in Quantum Electronics 11.4 (2005): 752-58

2. Farrow, D. C. and T. L. Vaughan. "Determinants of survival following the diagnosis of esophageal adenocarcinoma (United States)." Cancer Causes & Control 7.3 (1996)

3. American Cancer Society, Inc. © 2007

4. Blot, W. J., Devesa, S. S., Kneller, R. W., Fraumeni, J. F., "Rising Incidence of Adenocarcinoma of the Esophagus and Gastric Cardia." Jama—Journal of the American Medical Association 265.10 (1991)

5. Prach, A. T., MacDonald, T. A., Hopwood, D. A., Johnston, D. A., "Increasing incidence of Barrett's oesophagus: education, enthusiasm, or epidemiology?" Lancet 350.9082 (1997)

6. Tselepis, C., Perry, I., Jankowski, J., "Barrett's esophagus: Disregulation of cell cycling and intercellular adhesion in the metaplasia-dysplasia-carcinoma sequence." Digestion 61.1 (2000)

7. Mayo Clinic Foundation for Medical Education and Research© 1998-2007

8. Bergman, J. J. G. H., Tytgat, G. N. J., "New developments in the endoscopic surveillance of Barrett's oesophagus." Gut 54 (2005)

9. Boyce, H. W. "Barrett esophagus—Endoscopic findings and what to biopsy." Journal of Clinical Gastroenterology 38.5 (2003)

10. Peters, F. P., Kara, M. A., Rosmolen, W. D., ten Kate, F. J. W., Krishnadath, K. K., van Lanschot, J. J. B., Fockens, P., Bergman, J. J. G. H., "Stepwise radical endoscopic resection is effective for complete removal of Barrett's esophagus with early neoplasia: A prospective study." American Journal of Gastroenterology 101.7 (2006)

11. Bourg-Heckly, G., Blais, J., Padilla, J. J., Bourdon, O., Etienne, J., Guillemin, F., Lafay, L., "Endoscopic ultraviolet-induced autofluorescence spectroscopy of the esophagus: Tissue characterization and potential for early cancer diagnosis." Endoscopy 32.10 (2000)

12. Wallace, M. B., Sullivan, D., Rustgi, A. K., "Advanced imaging and technology in gastrointestinal neoplasia: Summary of the AGA-NCI Symposium Oct. 4-5, 2004." Gastroenterology 130.4 (2006)

13. Stolte, M. "The new Vienna classification of epithelial neoplasia of the gastrointestinal tract: advantages and disadvantages." Virchows Archiv 442.2 (2003)

14. Richards-Kortum, R., "Quantitative Optical Spectroscopy for Tissue Diagnosis," Annu. Rev. Phys. Chem., 47, 555-606 (1996)

15. Ramanujam, N. "Fluorescence spectroscopy of neoplastic and non-neoplastic tissues." Neoplasia 2.1-2 (2000)

16. Sun, Y., Liu, R., Elson, D S., Hollars, C. W., Jo, J. A., Jesung Park, J., Sun, Y., Marcu, L., "Simultaneous time- and wavelength-resolved fluorescence spectroscopy for near real-time tissue diagnosis" Optics Letters 33.6 (2008)

17. Georgakoudi, I., Jacobson, B. C., Van Dam, J., Backman, V., Wallace, M. B., Muller, M. G., Zhang, Q., Badizadegan, K., Sun, D., Thomas, G. A., Perelman, L. T., Feld, M. S., "Fluorescence, reflectance, and light-scattering spectroscopy for evaluating dysplasia in patients with Barrett's esophagus." Gastroenterology 120.7 (2001)

18. Tunnell, J. W., Desjardins, A. E., Galindo, L., Georgakoudi, I., Mcgee, S. A., Mirkovic, J., Mueller, M. G., Nazemi, J., Nguyen, F. T., Wax, A., Zhang, Q. G., Dasari, R. R., Feld, M. S., "Instrumentation for multi-modal spectroscopic diagnosis of epithelial dysplasia." Technology in Cancer Research & Treatment 2.6 (2003)

19. Kumar, S., C. Dunsby, C., De Beule, P. A. A., Owen, D. M., Anand, U., Lanigan, P. M. P., Benninger, R. K. P., Davis, D. M., Neil, M. A. A., Anand, P., Benham, C., Naylor, A., French, P. M. W., "Multifocal multiphoton excitation and time-correlated single photon counting detection for 3-D fluorescence lifetime imaging" Optics Express 15.20 (2007)

20. Das A, Sivak M V, Chak A, Wong R C K, Westphal V, Rollins A M, Willis J, Isenberg G, Izatt J A, "High-resolution endoscopic imaging of the GI tract: a comparative study of optical coherence tomography versus high-frequency catheter probe EUS." Gastrointenstinal Endoscopy 54.2 (2001)

21. Evans J. A., Poneros J. M., Bouma B. E., Bressner J., Halpern E. F., Shishkov M., Lauwers G. Y., Mino-Kenudson M., Nishioka N. S., Tearney G. J., "Optical coherence tomography to identify intramucosal carcinoma and high-grade dysplasia in Barrett's esophagus." Clinical Gastroenterology and Hepatology 4.1 (2006)

22. Curvers, W. L., Singh, R., Wong-Kee Song, L. M., Wolfsen, H. C., Ragunath, K., Wang, K., Wallace, M. B., Fockens, P., Bergman, J. J. G. H. M., "Endoscopic tri-modal imaging for detection of early neoplasia in Barrett's oesophagus: a multi-centre feasibility study using high-resolution endoscopy, autofluorescence imaging and narrow band imaging incorporated in one endoscopy system." Gut 57.2 (2008)

23. Anagnostopoulos, G. K., Yao, K., Kaye, P., Hawkey, C. J., Ragunath, K., "Novel endoscopic observation in Barrett's oesophagus using high resolution magnification endoscopy and narrow band imaging." Alimentary Pharmacology & Therapeutics 26.3 (2007)

24. Kara, M. A., Peters, F. P., Fockens, P., ten Kate, F. J. W., Bergman, J. J. G. H., "Endoscopic video-autofluorescence imaging followed by narrow band imaging for detecting early neoplasia in Barrett's esophagus." Gastrointestinal Endoscopy 64.2 (2006)

25. Gheorghe, C., Iacob, R, Becheanu, G., Dumbrava, M., "Confocal Endomicroscopy for in vivo Microscopic Analysis of Upper Gastrointestinal Tract Premalignant and Malignant Lesions" Journal of Gastrointestinal and Liver Diseases 17.1 (2008)

26. Wang, T. D., Friedland, S., Sahbaie, P., Soetikno, R., Hsiung, P. L., Liu, J. T. C., Crawford, J. M., Contag, C. H., "Functional Imaging of Colonic Mucosa With a Fibered Confocal Microscope for Real-Time In Vivo Pathology" Clinical Gastroenterology and Hepatology 5 (2007)

27. Kara, M. A., DaCosta, R. S., Streutker, C. J., Marcon, N. E., Bergman J. J. G. H. M., Wilson B. C.,"Characterization of tissue autofluorescence in Barrett's esophagus by confocal fluorescence microscopy." Diseases of the Esophagus 20.2 (2007)

28. Liu, J. T. C., Mandella, M. J., Friedland, S., Soetikno, R., Crawford, J. M., Contag, C. H., Kino, G. S., Wang, T. D., "Dual-axes confocal reflectance microscope for distinguishing colonic neoplasia", Journal of Biomedical Optics 11.5 (2006)

29. Ra, H., Piyawattanametha, W., Mandella, M. J., Hsiung, P. L., Hardy, J., Thomas D. Wang, T. D., Contag, C. H., Gordon S. Kino, G. S., Solgaard, O., "Three-dimensional in vivo imaging by a handheld dual-axes confocal microscope" Optics Express 16.10 (2008)

30. Tanbakuchi, A. A., Rouse, A. R., Hatch, K. D., Sampliner, R. E, Udovich, J. A., Gmitro, A. F., "Clinical evaluation of a confocal microendoscope system for imaging the ovary" Proceedings SPIE International Society of Optical Engineers, 6851 (2008)

31. Muldoon, T. J., Piercel, M. C., Nidal, D. L., Williams, M. D., Gillenwater, A., Richards-Kortum, R., "Subcellular-resolution molecular imaging within living tissue by fiber microendoscopy" Optics Express 15.25 (2007)

32. Licha, K. "Contrast agents for optical imaging." Contrast Agents Ii 222 (2002)

33. Zhuo, S., Chen, J., Jiang, X., Luo, T., Chen, R., Xie, S., Zou, Q., "Sequential Multitrack Nonlinear Ex vivo Imaging of Esophageal Stroma Based on Backscattered Second harmonic Generation and Two-photon Autofluorescence" Scanning 29 (2007)

34. Gono, K., Obi, T., Yamaguchi, M., Ohyama, N., Machida, H., Sano, Y., Yoshida, S., Hamamoto, Y., Endo, T., "Appearance of enhanced tissue features in narrow-band endoscopic imaging" Journal of Biomedical Optics 9.3 (2004)

35. Inoue, H., Sasajima, K., Kaga, M., Sugaya, S., Sato, Y., Wada, Y., Inui, M., Satodate, H., Kudo, S. E., Kimura, S., Hamatani, S., Shiokawa, A., "Endoscopic in vivo evaluation of tissue atypia in the esophagus using a newly designed integrated endocytoscope: a pilot trial." Endoscopy 38.9 (2006)

36. Sasajima, K., Kudo, S., Inoue, H., Takeuchi, T., Kashida, H., Hidaka, E., Kawachi, H., Sakashita, M., Tanaka, J., Shiokawa, A., "Real-time in vivo virtual histology of colorectal lesions when using the endocytoscopy system" Gastrointestinal Endoscopy 63.7 (2006)

Accordingly, the invention includes embodiments of a method, comprising: illuminating target tissue with ultraviolet (UV) light having a wavelength of less than 400 nm to produce fluorescense; providing imaging optics capable of producing microscopic resolution within a range from about 0.2 μm to about 5 μm, wherein a portion of said flourescense is directed toward said imaging optics to produce directed flourescense; optically collecting, with said imaging optics, substantially all of said directed fluorescense to produce collected fluorescense; and producing an image from said collected fluorescense. In the method, said fluorescence can comprise autofluorescense (AF). The method can further comprise visually displaying said image. In the method, said UV light can be selected to illuminate said target tissue to a depth consisting essentially of about 100 μm or less. In the method, said imaging optics can comprise a configuration selected from the group consisting of a wide-field microscope and wide-field microendoscope. In the method, the step of optically collecting substantially all of said directed fluorescense can be accomplished within a time duration of about 200 μs or less. The image can comprise an image spatial resolution, wherein said target tissue is within a living organism, wherein the step of optically collecting substantially all of said directed fluorescense is accomplished within a time duration that is no greater than the time it takes said target tissue to move, with respect to said imaging optics, the distance of said resolution of said image. The image can comprise a maximum image spatial resolution, wherein said target tissue is within a living organism, wherein the step of optically collecting substantially all of said directed fluorescense is accomplished within a time duration that is no greater than the time it takes said target tissue to move, with respect to said imaging optics, the distance of a desired said spatial resolution of said image, wherein said desired said spatial resolution is no greater than said maximum image spatial resolution. The UV light can comprise a wavelength selected from the group consisting of a wavelength within a range from about 180 nm to about 300 nm, a wavelength within a range from about 300 nm to about 320 nm, a wavelength within a range from about from about 320 nm to about 400 nm. The step of illuminating target tissue can be accomplished with a source of said UV light, wherein said UV light is coupled from said source into a fiber optic, wherein said fiber optic is operatively fixed within an endoscope, wherein said imaging optics are operatively fixed within said endoscope and wherein said imaging optics have an image plane thickness of less than about 100 μm. The target tissue can be selected from the group consisting of any tissue that is accessible by an endoscope within a living organism, any tissue within a living organism, any tissue within a living human being, cancer tissue, stomach tissue, oral tissue, kidney tissue, colon tissue, breast tissue, skin tissue, nail tissue, brain tissue, pancreas tissue, bile duct tissue, bladder tissue, esophagus tissue, bone marrow tissue, intestine tissue, oral tissue and lung tissue. In some cases, exogenous agent can be contacted to said target tissue, and in other cases, no exogenous agent has been contacted to said target tissue. The step of producing an image from said directed fluorescense can be accomplished without the use of a spatial filter. The step of optically collecting substantially all of said directed fluorescense to produce collected fluorescense can include collecting said directed fluorescense for an exposure time of about or less than a desired image resolution divided by the relative velocity of said target tissue with respect to said imaging optics. The method can further comprise taking a biopsy of said target tissue when said image shows suspect tissue selected from the group consisting of normal columnar mucosa having a honeycomb like pattern with goblet cells, a glandular crypt which appears as one or more depressions or large dark holes on the surface of columnar epithelium, dysplastic epithelium where the surface is includes multiple papillary, villiform or cauliform structures, disorganized tissue with loss of the specific cellular outline patterns characteristic of normal squamous or columnar epithelia and epithelial mucosa with abnormal blood vascular pattern or angiogenesis associated with malignant neoplasia. The method can further comprise therapeutically treating said target tissue when said image shows suspect tissue selected from the group consisting of normal columnar mucosa having a honeycomb like pattern with goblet cells, a glandular crypt which appears as one or more depressions or large dark holes on the surface of columnar epithelium, dysplastic epithelium where the surface is includes multiple papillary, villiform or cauliform structures, disorganized tissue with loss of the specific cellular outline patterns characteristic of normal squamous or columnar epithelia and epithelial mucosa with abnormal blood vascular pattern or angiogenesis associated with malignant neoplasia. The method can further comprise identifying said target tissue as suspected diseased tissue when said image shows a tissue image selected from the group consisting of normal columnar mucosa having a honeycomb like pattern with goblet cells, a glandular crypt which appears as one or more depressions or large dark holes on the surface of columnar epithelium, dysplastic epithelium where the surface is includes multiple papillary, villiform or cauliform structures, disorganized tissue with loss of the specific cellular outline patterns characteristic of normal squamous or columnar epithelia and epithelial mucosa with abnormal blood vascular pattern or angiogenesis associated with malignant neoplasia. The collected flourescense can substantially comprise said directed flourescense less the amount of said directed flourescense attenuated by said imaging optics. The UV light can comprises at least two wavelengths, wherein the step of optically collecting substantially all of said directed fluorescense can be accomplished within a time duration of about 200 μs or less. Embodiments of the invention include apparatuses configured to accomplish the above stated methods.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. A method, comprising:

illuminating target tissue with ultraviolet (UV) light having a wavelength of less than 400 nm to produce fluorescense;

providing imaging optics capable of producing microscopic resolution within a range from about 0.2 μm to about 5 μm, wherein a portion of said flourescense is directed toward said imaging optics to produce directed flourescense;

optically collecting, with said imaging optics, substantially all of said directed fluorescense to produce collected fluorescense; and producing an image from said collected fluorescense; wherein said image comprises an image spatial resolution, wherein said target tissue is within a living organism, wherein the step of optically collecting substantially all of said directed fluorescense is accomplished within a time duration that is no greater than the time it takes said target tissue to move, with respect to said imaging optics, the distance of said image spatial resolution.

2. The method of claim 1, wherein said fluorescence comprises autofluorescense (AF).

3. The method of claim 1, further comprising visually displaying said image.

4. The method of claim 1, wherein said UV light is selected to illuminate said target tissue to a depth consisting essentially of about 100 μm or less.

5. The method of claim 1, wherein said imaging optics comprise a configuration selected from the group consisting of a wide-field microscope and wide-field microendoscope.

6. The method of claim 1, wherein the step of optically collecting substantially all of said directed fluorescense is accomplished within a time duration of about 200 μs or less.

7. The method of claim 1, wherein said image comprises a maximum image spatial resolution, wherein said target tissue is within a living organism, wherein the step of optically collecting substantially all of said directed fluorescense is accomplished within a time duration that is no greater than the time it takes said target tissue to move, with respect to said imaging optics, the distance of a desired said spatial resolution of said image, wherein said desired said spatial resolution is no greater than said maximum image spatial resolution.

8. The method of claim 1, wherein said UV light comprises a wavelength selected from the group consisting of a wavelength within a range from about 180 nm to about 300 nm, a wavelength within a range from about 300 nm to about 320 nm, a wavelength within a range from about from about 320 nm to about 400 nm.

9. The method of claim 1, wherein the step of illuminating target tissue is accomplished with a source of said UV light, wherein said UV light is coupled from said source into a fiber optic, wherein said fiber optic is operatively fixed within an endoscope, wherein said imaging optics are operatively fixed within said endoscope and wherein said imaging optics have an image plane thickness of less than about 100 μm.

10. The method of claim 1, wherein said target tissue is selected from the group consisting of any tissue that is accessible by an endoscope within a living organism, any tissue within a living organism, any tissue within a living human being, cancer tissue, stomach tissue, oral tissue, kidney tissue, colon tissue, breast tissue, skin tissue, nail tissue, brain tissue, pancreas tissue, bile duct tissue, bladder tissue, esophagus tissue, bone marrow tissue, intestine tissue, oral tissue and lung tissue.

11. The method of claim 2, wherein exogenous agent has been contacted to said target tissue.

12. The method of claim 2, wherein no exogenous agent has been contacted to said target tissue.

13. The method of claim 1, wherein the step of producing an image from said directed fluorescense is accomplished without the use of a spatial filter.

14. The method of claim 1, wherein the step of optically collecting substantially all of said directed fluorescense to produce collected fluorescense includes collecting said directed fluorescense for an exposure time of about or less than a desired image resolution divided by the relative velocity of said target tissue with respect to said imaging optics.

15. The method of claim 2, further comprising taking a biopsy of said target tissue when said image shows suspect tissue selected from the group consisting of normal columnar mucosa having a honeycomb like pattern with goblet cells, a glandular crypt which appears as one or more depressions or large dark holes on the surface of columnar epithelium, dysplastic epithelium where the surface is includes multiple papillary, villiform or cauliform structures, disorganized tissue with loss of the specific cellular outline patterns characteristic of normal squamous or columnar epithelia and epithelial mucosa with abnormal blood vascular pattern or angiogenesis associated with malignant neoplasia.

16. The method of claim 2, further comprising therapeutically treating said target tissue when said image shows suspect tissue selected from the group consisting of normal columnar mucosa having a honeycomb like pattern with goblet cells, a glandular crypt which appears as one or more depressions or large dark holes on the surface of columnar epithelium, dysplastic epithelium where the surface is includes multiple papillary, villiform or cauliform structures, disorganized tissue with loss of the specific cellular outline patterns characteristic of normal squamous or columnar epithelia and epithelial mucosa with abnormal blood vascular pattern or angiogenesis associated with malignant neoplasia.

17. The method of claim 2, further comprising identifying said target tissue as suspected diseased tissue when said image shows a tissue image selected from the group consisting of normal columnar mucosa having a honeycomb like pattern with goblet cells, a glandular crypt which appears as one or more depressions or large dark holes on the surface of columnar epithelium, dysplastic epithelium where the surface is includes multiple papillary, villiform or cauliform structures, disorganized tissue with loss of the specific cellular outline patterns characteristic of normal squamous or columnar epithelia and epithelial mucosa with abnormal blood vascular pattern or angiogenesis associated with malignant neoplasia.

18. The method of claim 1, wherein said collected flourescense substantially comprises said directed flourescense less the amount of said directed flourescense attenuated by said imaging optics.

19. The method of claim 1, wherein said UV light comprises at least two wavelengths, wherein the step of optically collecting substantially all of said directed fluorescense is accomplished within a time duration of about 200 μs or less.

20. An apparatus, comprising:

means for illuminating target tissue with ultraviolet (UV) light having a wavelength of less than 400 nm to produce fluorescense;

imaging optics capable of producing microscopic resolution within a range from about 0.2 μm to about 5 μm, wherein said imaging optics are fixed such that a portion of said flourescense is directed toward said imaging optics to produce directed flourescense, wherein said imaging optics substantially collect all of said directed fluorescense to produce collected fluorescense; and means for producing an image from said collected fluorescense; wherein said imaging optics produce an image spatial resolution that is no less than the time it takes said target tissue to move, with respect to said imaging optics, the distance of said image spatial resolution.

21. The apparatus of claim 20, wherein said fluorescence comprises autofluorescense (AF).

22. The apparatus of claim 20, wherein said UV light can be selected to illuminate said target tissue to a depth consisting essentially of about 100 μm or less.

23. The apparatus of claim 20, wherein said imaging optics comprise a configuration selected from the group consisting of a wide-field microscope and wide-field microendoscope.

24. The apparatus of claim 20, wherein said imaging optics substantially collect all of said directed fluorescense within a time duration of about 200 μs or less.

25. The apparatus of claim 20, wherein said UV light comprises a wavelength selected from the group consisting of a wavelength within a range from about 180 nm to about 300 nm, a wavelength within a range from about 300 nm to about 320 nm, a wavelength within a range from about from about 320 nm to about 400 nm.

26. The apparatus of claim 20, wherein said means for illuminating target tissue is accomplished with a source of said UV light, said apparatus further comprising a fiber optic, wherein said UV light is coupled from said source into said fiber optic, said apparatus further comprising an endoscope, wherein said fiber optic is operatively fixed within said endoscope, wherein said imaging optics are operatively fixed within said endoscope and wherein said imaging optics have an image plane thickness of less than about 100 μm.

27. The apparatus of claim 20, wherein said means for producing an image from said directed fluorescense is accomplished without the use of a spatial filter.

* * * * *